United States Patent [19]

Holtkamp, Sr.

[11] Patent Number: Plant 6,527

[45] Date of Patent: Jan. 10, 1989

[54] AFRICAN VIOLET PLANT NAMED LEO

[75] Inventor: Reinhold Holtkamp, Sr., Isselburg, Fed. Rep. of Germany

[73] Assignee: Gessellschaftsvertrag uber die Erfindergemeinschaft "Optimara", Rees Haften, Fed. Rep. of Germany

[21] Appl. No.: 56,145

[22] Filed: Jun. 1, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

An African violet plant named Leo, characterized by its long-lasting, non-dropping, double, solid blue flowers with frilled edges, strong upright flower stems, curving toward the center; profuse flowering; vigorous growth habit; very attractive girl-type leaves, wavy, strongly serrated with a white to light green center; and long lasting and non-dropping flowering habit.

1 Drawing Sheet

The present invention comprises a new and distinct cultivar of African violet plant, botanically known as *Saintpaulia ionantha,* and hereinafter referred to by the cultivar name Leo.

The new cultivar was referred to during the breeding and selection process by the designation G12/42, and is a product of a planned breeding program. The new cultivar was originated from a cross made by applicant in a controlled breeding program in Haffen, Federal Republic of Germany. The female, or seed parent was a cultivar designated XIX4158 red. The male, or pollen parent was a cultivar designated 67 red girl.

Leo was discovered and selected by me as a flowering plant within the progeny of the stated cross in a controlled environment in Haffen, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Leo has not been observed under all possible environmental conditions. The phenotype may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Leo which in combination distinguish this African violet as a new and distinct cultivar:

1. Strong upright flower stems curving toward the center.
2. Long-lasting non-dropping, double, solid blue flowers with frilled edges.
3. Profuse flowering.
4. Each plant carries 8 and more upright flower stems, each of which carries 9 to 12 flowers.
5. Vigorous grower.
6. Plant saleable 9–10 weeks after potting.
7. Seed capsules push slightly through.
8. Very attractive girl-type leaf, wavy, strongly serrated with a white to light green center.

9. After maturity the flowers dry off and remain on the peduncle without becoming infected by botrytis.
10. The anthers are almost completely covered up by the double flowers.

The closest known variety is Orlando, whose girl-type leaves and flower color are similar to Leo. Differences between Orlando and Leo are in the greater number of petals on each flower in Leo, and the color and serration of the leaves of Leo.

The accompanying color photographic drawing shows a typical specimen plant of the new cultivar. The colors appearing in the photograph are as true as possible with color illustrations of this type.

In the following description, color references are made to The Royal Horticultural Society Colour Chart (RHS), except where general colors of ordinary significance are referred to. Color values were taken under natural light conditions at approximately 2.00 p.m. in Nashville, Tenn. Under cooler growing conditions and more intensive lighting, the blue color becomes more intense.

Botanical classification: *Saintpaulia ionantha,* ; Ramat., cv. Leo.

Parentage:

*Male parent.*—67 Red girl.

*Female parent.*—XIX 4156 Red.

Propagation: The new cultivar holds its distinguishing characteristics through successive propagations by leaf cuttings and by division of shoots.

Plant: From 8 cm to 10 cm tall when grown in pots, and approximately 18–20 cm in diameter when fully grown.

*Leaves.*—Shape: Round to heart-shaped, girl-type, curled up at center. Diameter: 65–70 mm. Texture: Velvety. Ribs and veins: Upperside visible, light green towards the center; underside well pronounced, very light green and shiny, purplish on the very young leaves. Color (upper side): Green 137 between A and B. Color (under side): Green 138C. Petioles: Strong, upright, light green with purplish red touch on side towards flowers, hairy.

*Flowers.*—Buds: Green-purple variegated, ball-shaped, 6–8 mm just before opening. Sepals: Five (5) in number, green with brownish touch. Calyx: Funnel-shaped, flat. Aspect: Spear-shaped, hairy. Peduncle: Strong, upright, green with purplish red touch, hairy.

*Individual flowers.*—Size: 35 to 40 mm. Shape: Double, violet-shaped with frilled edges; 3 large and 2 small petals plus up to 5–6 additional small petals; round, with wavy, frilled edges. Color (upper side): Violet blue 89B. Color (under side): Violet blue between 89C and D. Borne: Each flower stem carries 9–12 and more flowers on strong, upright peduncles that are free standing above the leaves and that are curving toward the center of the plant. Corolla: Compact flower head, free-standing above the leaves. Flowering habit: Flowers 9–10 weeks after potting.

*Reproductive organs.*—Stamens: Two (2) in number. Anthers: Two, composed of 4 anther cells. Filaments: 4 mm long, yellowish green with blue edges. Pollen Color: Yellow 7A. Styles: 6 mm, purplish blue, with a light green, hairy base of ovary.

*Roots.*—Normally developed, white when young, turning slightly brownish when older.

Disease resistance: Good.

General observations:

Leo has a very attractive appearance due to its medium green, strongly serrated, wavy, girl-type leaves and violet blue flower color. A tight and very full bouquet of flowers are formed on strong peduncles, free-standing above the leaves, with the flowers being double with frilled edges. The bright yellow anthers are often visible because the many small curly petals cover them up. The flowers are long-lasting and non-dropping.

I claim:

1. A new and distinct cultivar of African violet named Leo, as described and illustrated, and particularly characterized by its long-lasting, non-dropping, double, solid blue flowers with frilled edges; strong upright flower stems, curving toward the center; profuse flowering; vigorous growth habit; very attractive girl-type leaves, wavy, strongly serrated with a white to light green center; and long lasting and non-dropping flowering habit.

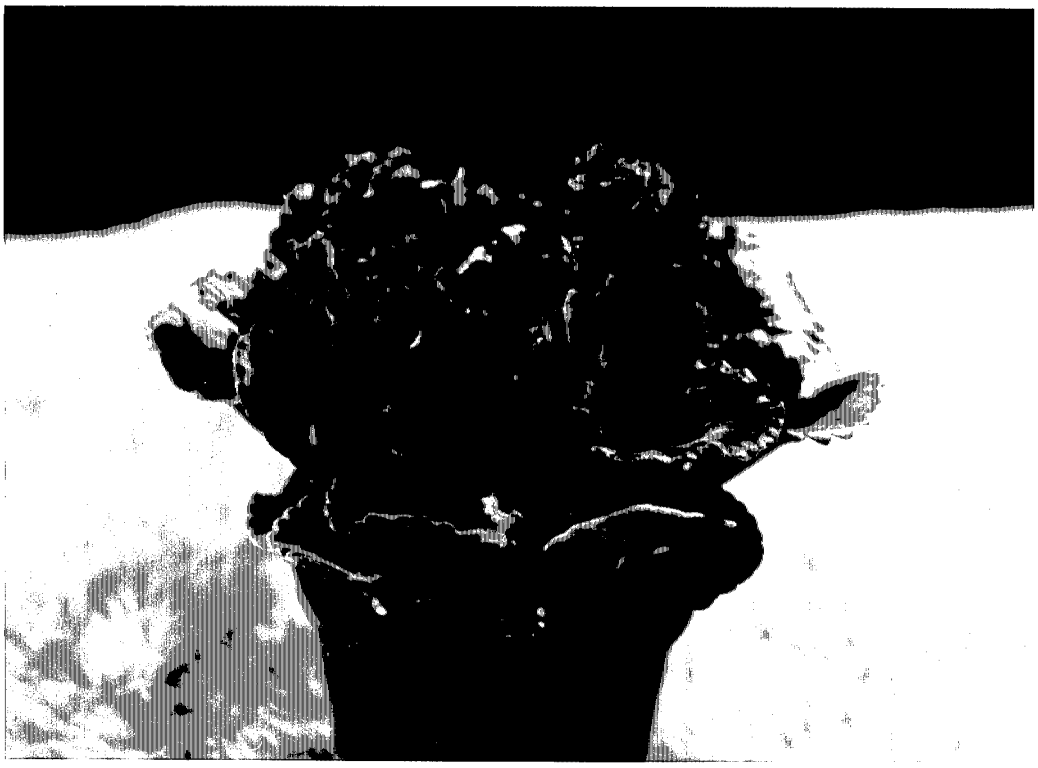

* * * * *